United States Patent [19]

Bentley et al.

[11] Patent Number: 4,723,006
[45] Date of Patent: Feb. 2, 1988

[54] PROCESS FOR 4,6-DI-SUBSTITUTED 2-AMINOPYRIMIDINES

[75] Inventors: Robert L. Bentley, Manchester; Brian Tuck, Stockport, both of England

[73] Assignee: Ciba-Geigy Corporation, Ardsley, N.Y.

[21] Appl. No.: 821,081

[22] Filed: Jan. 21, 1986

Related U.S. Application Data

[60] Division of Ser. No. 733,548, May 13, 1985, abandoned, which is a continuation of Ser. No. 541,610, Oct. 13, 1983, abandoned.

[30] Foreign Application Priority Data

Oct. 15, 1982 [GB] United Kingdom ............... 8229560

[51] Int. Cl.$^4$ ........................................... C07D 239/47
[52] U.S. Cl. .................... 544/320; 544/326; 544/330; 544/331; 544/334
[58] Field of Search ................ 544/320, 330

[56] References Cited

U.S. PATENT DOCUMENTS 2,658,895 11/1953 Ballard et al. ................ 544/242
3,050,523 8/1962 Erner et al. ................... 544/242

FOREIGN PATENT DOCUMENTS 0070804 1/1983 European Pat. Off.
1034608 6/1966 United Kingdom.
1409034 10/1975 United Kingdom.

OTHER PUBLICATIONS

Bergmann, et al.; J. Chem. Soc., (1959), pp. 3278–3285.
Elderfield, "Heterocyclic Compounds", vol. 6, (1957), pp. 265 & 268–270,; John Wiley & Sons; N.Y.

Primary Examiner—Joseph Paul Brust
Attorney, Agent, or Firm—Edward McC. Roberts; Kevin T. Mansfield

[57] ABSTRACT

New compounds useful as intermediates for biologically-active compounds have the formula I

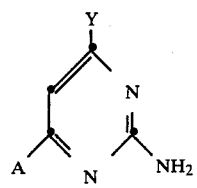

wherein Y is a group having the formula —CH$_2$X in which X is F, Cl, or Br, or Y is a group having the formula

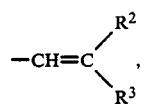

in which $R^2$ is F, Cl or Br and $R^3$ is H, F, Cl, Br or a group having the formula —CR$^4$R$^5$R$^6$, in which R$^4$, R$^5$ and R$^6$, independently, are F, Cl or Br; A is H, OH, SH, F, Cl, Br or a group —OR$^7$ or —SR$^7$ in which R$^7$ is C$_1$–C$_4$ straight- or branched chain alkyl, C$_{2-4}$ straight- or branched chain alkyl substituted with 1 to 3 F, Cl or Br atoms, or A is a group —NR$^8$R$^9$ in which R$^8$ and R$^9$, independently, are H, C$_1$–C$_4$ straight- or branched chain alkyl or C$_3$–C$_4$ alkenyl, or R$^8$ and R$^9$ together may form a C$_3$–C$_7$ polymethylene chain, which is optionally interrupted by an oxygen atom; as well as salts of compounds of formula I with acids; provided that: when Y is CH$_2$F, then A is as hereinbefore defined other than OH, Cl or OCH$_3$.

5 Claims, No Drawings

PROCESS FOR 4,6-DI-SUBSTITUTED 2-AMINOPYRIMIDINES

This is a divisional of application Ser. No. 733,548 filed on May 13, 1985, now abandoned which is a continuation of application Ser. No. 541,610, filed Oct. 13, 1983, now abandoned.

The present invention relates to new chemical compounds, in particular 2-aminopyrimidines, to processes for their production and to their use as intermediates for biologically-active compounds.

According to the method described in "The Chemistry of Heterocyclic Compounds", Vol. XVI, Interscience Publishers, New York; 2-amino-4-hydroxypyrimidines are produced by reacting the appropriate beta-keto ester derivative with guanidine. Moreover, E. D. Bergmann et al. J. Chem Soc. 3278 (1959) disclose the reaction of guanidine with the ethyl ester of gamma-fluoro-acetoacetic acid to give quantitative yields of the compound of formula

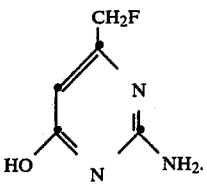

The art-skilled would, therefore, have had reason to expect that the reaction of guanidine with the ethyl ester of gamma-chloro-acetoacetic acid would provide good yields of the compound of formula

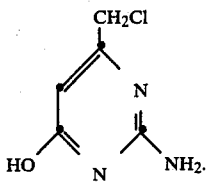

While this reaction has not been reported in the literature, we have found that only very low yields of the expected product are obtained.

Surprisingly, we have now found that, by reacting gamma-haloacetoacetyl halides with guanidine (or a salt thereof) good yields of certain 2-amino-4,6-disubstituted pyrimidine compounds, most of which are new compounds, are obtained.

It is therefore an object of the present invention to provide new 2-amino-4,6-disubstituted pyrimidines, and processes for producing these new compounds.

According to the present invention, there are provided compounds having the formula

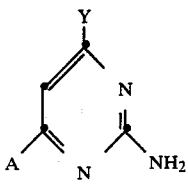

I wherein Y is a group having the formula —CH$_2$X in which X is F, Cl, or Br, or Y is a group having the formula

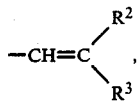

in which R$^2$ is F, Cl or Br and R$^3$ is H, F, Cl, Br or a group having the formula —CR$^4$R$^5$R$^6$, in which R$^4$, R$^5$ and R$^6$, independently, are F, Cl or Br; A is H, OH, SH, F, Cl, Br or a group —OR$^7$ or —SR$^7$ in which R$^7$ is C$_1$–C$_4$ straight- or branched chain alkyl, C$_{2-4}$ straight- or branched chain alkyl substituted with 1 to 3 F, Cl or Br atoms, or A is a group —NR$^8$R$^9$ in which R$^8$ and R$^9$, independently, are H, C$_1$–C$_4$ straight- or branched chain alkyl or C$_3$–C$_4$ alkenyl, or R$^8$ and R$^9$ together may form a C$_3$–C$_7$ polymethylene chain, which is optionally interrupted by an oxygen atom; as well as salts of compounds of formula I with acids; provided that: when Y is CH$_2$F, then A is as hereinbefore defined other than OH, Cl or OCH$_3$.

Examples of acids which form salts with the compounds of formula I include both inorganic acids, e.g. hydrochloric-, sulphuric-, perchloric- and phosphoric acids, and organic acids, e.g. methane-sulphonic-, trifluoroacetic- and para-toluene sulphonic acids.

It will be appreciated that, when substituent A is OH or SH, the corresponding compounds of formula I may exist in the following tautomeric forms Ia and Ib

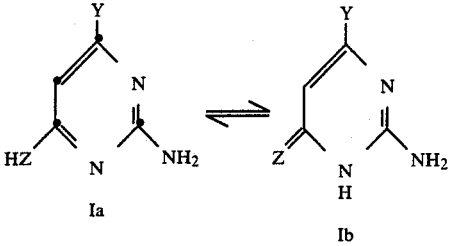

wherein Z is O or S.

Such compounds of formula I are amphoteric and also form salts with bases, e.g. the hydroxides of the alkali metals.

When Y is a group of formula —CH=CR$^2$R$^3$ in which R$^2$ and R$^3$ have their previous significance, examples of such groups Y include —CH=CF$_2$, —CH=CCl$_2$, —CH=CBr$_2$, —CH=C(Cl)CF$_3$, —CH=C(Cl)Br and —CH=C(Cl)F.

When A is a group —OR$^7$ or —SR$^7$, wherein R$^7$ has its previous significance, examples of such groups A include OCH$_3$, OC$_2$H$_5$, OCH$_2$CH$_2$CH$_3$, OCH(CH$_3$)$_2$, OCH$_2$CH$_2$CH$_2$CH$_3$, OCH$_2$CH(CH$_3$)$_2$, OCH$_2$CH$_2$Cl, OCH$_2$CF$_3$, OCH$_2$CH$_2$Br, SCH$_3$, SC$_2$H$_5$, SCH$_2$CH$_2$CH$_3$, SCH(CH$_3$)$_2$, SCH$_2$CH(CH$_3$)$_2$, SCH$_2$CH$_2$CH$_2$CH$_3$, SCH$_2$CH$_2$Cl, and SCH$_2$CH$_2$Br.

When A is a group —NR$^8$R$^9$ in which R$^8$ and R$^9$ have their previous significance, examples of such groups A include NH$_2$, NHCH$_3$, N(CH$_3$)$_2$, NHC$_2$H$_5$, N(CH$_3$)C$_2$H$_5$, NHCH$_2$CH$_2$CH$_3$, NH(CH$_2$CH$_3$)$_2$, N[CH(CH$_3$)$_2$]$_2$, N(CH$_2$CH$_2$CH$_3$)$_2$, NHCH$_2$CH=CH$_2$, N(CH$_2$CH=CH$_2$)$_2$,

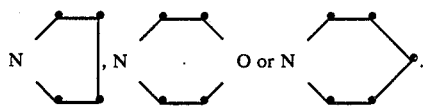

Preferred compounds of formula I are those wherein Y is CH₂X in which X has its previous significance, or Y is —CH═CR²R³ in which R² and R³ are Br or, especially Cl, and A has its previous significance.

More preferred are those compounds of formula I, wherein Y is CH₂X in which X is F or Cl, or Y is —CH═CCl₂, and A is H, OH, SH, F, Cl or Br or a group OR⁷ or SR⁷ in which R⁷ is methyl, ethyl or 2,2,2-trifluoroethyl or A is a group NR⁸R⁹ in which R⁸ and R⁹, independently, are hydrogen, methyl or ethyl.

Still more preferred compounds of formula I are those wherein Y is CH₂X in which X is F or Cl and A is F, Cl, Br or a group OR⁷ or NR⁸R⁹ in which R⁷ is methyl, ethyl or 2,2,2-trifluoroethyl and R⁸ and R⁹, independently, are hydrogen or methyl.

The new compounds of the formula I are useful as intermediates for the preparation of biologically active compounds. For example, they can be reacted with a phenylsulfonylisocyanate which is optionally substituted on the phenyl ring to form the corresponding N-phenylsulfonyl-N'-pyrimidin-2-yl ureas which possess excellent herbicidal activity.

Specific examples of compounds of formula I, and their salts, are set out as follows in tabular form:

| Compound | Y | A |
|---|---|---|
| 1 | CH₂F | H |
| 2 | CH₂F | OH |
| 3 | CH₂F | SH |
| 4 | CH₂F | F |
| 5 | CH₂F | Cl |
| 6 | CH₂F | Br |
| 7 | CH₂F | OCH₃ |
| 8 | CH₂F | OCH₂CH₃ |
| 9 | CH₂F | OCH₂CH(CH₃)₂ |
| 10 | CH₂F | OCHF₂ |
| 11 | CH₂F | OCH₂CF₃ |
| 12 | CH₂F | SCH₃ |
| 13 | CH₂F | SCH(CH₃)₂ |
| 14 | CH₂F | SCH₂CF₃ |
| 15 | CH₂F | NH₂ |
| 16 | CH₂F | NHCH₃ |
| 17 | CH₂F | N(CH₃)₂ |
| 18 | CH₂F | N(CH₃)₂ Hydrochloride |
| 19 | CH₂F | N(CH₃)₂ Sulphate |
| 20 | CH₂F | (N-pyrrolidinyl) |
| 21 | CH₂Cl | H |
| 22 | CH₂Cl | OH |
| 23 | CH₂Cl | F |
| 24 | CH₂Cl | Cl (and hydrochloride salt) |
| 25 | CH₂Cl | Br |
| 26 | CH₂Cl | OCH₃ |
| 27 | CH₂Cl | OCH₂CH₂Cl |
| 28 | CH₂Cl | OCH₂CF₃ |
| 29 | CH₂Cl | OCH₂CH₂CH₂CH₃ |
| 30 | CH₂Cl | SH |
| 31 | CH₂Cl | SCH₂CH₃ |
| 32 | CH₂Cl | SCH(CH₃)₂ |
| 33 | CH₂Cl | SCH₂CF₃ |
| 34 | CH₂Cl | NH₂ |
| 35 | CH₂Cl | NHCH₃ |
| 36 | CH₂Cl | NHCH₂CH₃ |
| 37 | CH₂Cl | NHCH₂CH═CH₂ |
| 38 | CH₂Cl | N(CH₂CH₃)₂ |
| 39 | CH₂Cl | N(CH₃)₂ |
| 40 | CH₂Cl | N[CH(CH₃)₂]₂ |
| 41 | CH₂Cl | N(CH₂CH═CH₂)₂ |
| 42 | CH₂Cl | (N-morpholinyl) |
| 43 | CH₂Br | H |
| 44 | CH₂Br | OH |
| 45 | CH₂Br | F |
| 46 | CH₂Br | Cl |
| 47 | CH₂Br | Br |
| 48 | CH₂Br | OCH₂CH₂CH₃ |
| 49 | CH₂Br | SH |
| 50 | CH₂Br | SCH₂CH₃ |
| 51 | CH₂Br | NHCH₂CH₂CH₃ |
| 52 | CH₂Br | N(CH₂CH₂CH₃)₂ |
| 53 | CH═CF₂ | H |
| 54 | CH═CF₂ | OH |
| 55 | CH═CF₂ | F |
| 56 | CH═CF₂ | OCH₃ |
| 57 | CH═CF₂ | SH |
| 58 | CH═CF₂ | SCH₃ |
| 59 | CH═CF₂ | NHCH(CH₃)₂ |
| 60 | CH═CF₂ | N[CH₂CH(CH₃)₂]₂ |
| 61 | CH═CCl₂ | H |
| 62 | CH═CCl₂ | OH |
| 63 | CH═CCl₂ | OCH₃ |
| 64 | CH═CCl₂ | OCH₂CH₂Cl |
| 65 | CH═CCl₂ | OCH₂CF₃ |
| 66 | CH═CCl₂ | OCH(CH₃)₂ |
| 67 | CH═CCl₂ | SH |
| 68 | CH═CCl₂ | SCH₂CH₃ |
| 69 | CH═CCl₂ | SCH₂CH(CH₃)₂ |
| 70 | CH═CCl₂ | Cl |
| 71 | CH═CCl₂ | SCH₂CF₃ |
| 72 | CH═CCl₂ | NH₂ |
| 73 | CH═CCl₂ | NHCH₃ |
| 74 | CH═CCl₂ | N(CH₃)₂ |
| 75 | CH═CCl₂ | NHCH₂CH₃ |
| 76 | CH═CCl₂ | N(CH₂CH₃)₂ |
| 77 | CH═CCl₂ | N(CH₃)(CH₂CH₃) |
| 78 | CH═CCl₂ | NHCH₂CH═CH₂ |
| 79 | CH═CCl₂ | N(CH₂CH═CH₂)₂ |
| 80 | CH═CCl₂ | (N-piperidinyl) |
| 81 | CH═CBr₂ | H |
| 82 | CH═CBr₂ | OH |
| 83 | CH═CBr₂ | F |
| 84 | CH═CBr₂ | Cl |
| 85 | CH═CBr₂ | Br |
| 86 | CH═CBr₂ | OCH₂CH₃ |
| 87 | CH═CBr₂ | OCH₂CH₂CH₃ |
| 88 | CH═CBr₂ | OCH(CH₃)₂ |
| 89 | CH═CBr₂ | OCH₂CF₃ |
| 90 | CH═CBr₂ | SH |
| 91 | CH═CBr₂ | SCH₃ |
| 92 | CH═CBr₂ | NHCH₂CH₂CH₃ |
| 93 | CH═CBr₂ | N(CH₂CH₂CH₃)₂ |
| 94 | CH═C(Cl)(CF₃) | OH |

The present invention also provides a first process for producing a compound of formula I'

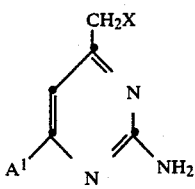

wherein A¹ is the same as A as hereinbefore defined or is $OCH_3$ or $SCH_3$ substituted by 1 to 3 Cl, Br or F atoms, comprising:

(a) reacting, at elevated temperature, a compound having the formula II $XCH_2COCH_2COX^o$    II wherein X and $X^o$ independently, are F, Cl or Br, and $X^o$ is especially Cl, with guanidine or a guanidine salt, preferably guanidine hydrochloride, to produce a compound having the formula III

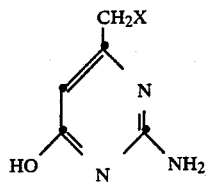

or the corresponding salt thereof, wherein X has its previous significance;

(b) optionally reacting the compound of formula III with an halogenating agent to produce a compound having the formula IV

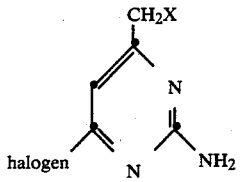

wherein X has its previous significance and halogen is F, Cl or Br; and (c) optionally reacting compound IV with a reagent capable of converting the halogen substituent into a different substituent A¹, as hereinbefore defined.

Conveniently, the acid halide compound of formula II is heated with an excess of a guanidine salt, e.g. the hydrochloride, preferably in the absence of a solvent, at a temperature within the range of from 50° to 200° C., especially from 100° to 120° C. The compound of formula III is then obtained as its salt, e.g. the hydrochloride salt, from which the free base may be liberated by neutralisation.

The starting materials of formula II are compounds which are known per se, or may be prepared by methods which are well-known to the art-skilled. In particular, the preparation of the compound $Cl.CH_2.COCH_2COCl$ is described by C. D. Hurd and J. L. Abernethy, JACS, 1940, 62, 1147.

In a second process according to the invention:
(a) a beta-lactone having the formula V

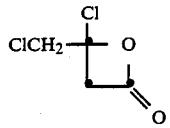

is reacted with guanidine, or a guanidine salt, preferably guanidine hydrochloride, at elevated temperature, to produce a compound having the formula IIIa:

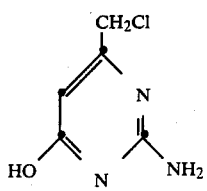

or the corresponding salt thereof, and optionally:

(b) the compound of formula IIIa is reacted with a halogenating agent to produce a compound of formula IVa

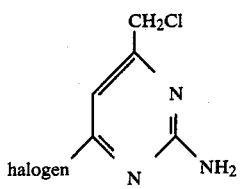

wherein halogen has its previous significance; and optionally (c) reacting the compound of formula IVa with a reagent capable of converting the ring halogen substituent into a different substituent A¹, as hereinbefore defined.

The first stage of this second process according to the present invention is conveniently effected by heating a mixture of the lactone of formula V with an excess of a guanidine salt, e.g. guanidine hydrochloride, preferably in the absence of a solvent, at a temperature within the range of from 50° to 200° C., preferably from 100° to 120° C. The product of formula IIIa is obtained as its salt, from which the free base may be liberated by neutralisation with a basic substance such as sodium bicarbonate.

The starting materials of formula V may be produced by reacting a compound having the formula VI

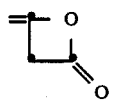

with sulphuryl chloride, in the presence of a radical initiator.

In a third process according to the invention, compounds of formula I''

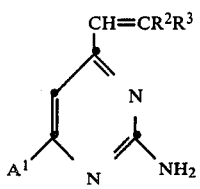

I″ wherein A¹ is the same as A or OCH₃ or SCH₃ substituted by 1 to 3 Cl, Br of F atoms are produced by:
(a) reacting a lactone of formula VII

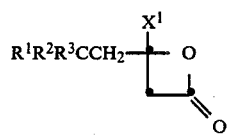

VII wherein R¹ is F, Cl or Br, R² and R³ have their previous significance and X¹ is Cl, Br or I with the priviso that when X¹ is Cl, none of R¹, R², R³, R⁴, R⁵ and R⁶ can be Br, with guanidine or a guanidine salt, preferably the hydrochloride, at elevated temperature, to produce a compound having the formula VIII

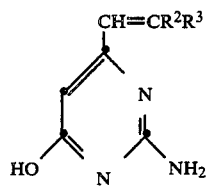

VIII or the corresponding salt thereof, wherein R² and R³ have their previous significance; and (b) optionally reacting the compound of formula VIII with an halogenating agent to produce a compound having the formula IX

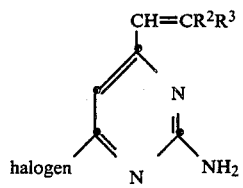

IX wherein halogen is F, Cl or Br, R² and R³ have their previous significance; and (c) optionally reacting the compound of formula IX with a reagent capable of converting the ring halogen substituent into a different substituent A¹, as hereinbefore defined.

The third process of the invention is conveniently effected by heating a mixture of lactone VII with an excess of guanidine or a guanidine salt, preferably the hydrochloride, at 50° to 200° C., especially 100° to 160° C., for at least one hour. Compound VIII is obtained as its salt from which the free base may be obtained by neutralisation with a basic substance such as sodium acetate.

The starting materials of formula VII are described in French Patent Specification No. 2 479 215.

The individual optional process stages (b) are conveniently effected by reacting, at elevated temperature, the corresponding starting material (compound III, IIIa or VIII) with an halogenating agent conventionally used for replacing an OH group by a halogen atom, e.g. phosphorus halides, phosphorous oxyhalides and sulphur oxyhalides, in particular phosphorus tri- and pentachloride, phosphorus tri- and pentabromide, phosphoryl chloride, phosphoryl bromide, thionyl chloride or thionyl bromide; as well as cyanuric fluoride.

The individual optional process stages (c) each involve well-known conversion techniques, for instance the reaction of the respective starting materials IV, IVa or IX, in which A¹ is F, Cl or Br, with a nucleophilic reagent, e.g. alkoxides and amines capable of displacing the halogen group.

Further illustrative, non-limiting reaction schemes for the respective optional steps (c) are outlined below:

wherein Y, R⁷, R⁸ and R⁹ have their previous significance;

wherein A is Cl or Br and X is Cl or Br;

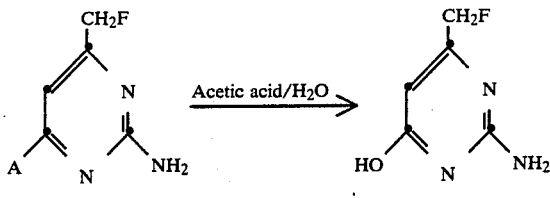

wherein A is F, Cl or Br.

The present invention is further illustrated by the following Examples, in which parts and percentages shown therein are by weight.

EXAMPLE 1

2-Amino-4-chloromethyl-6-hydroxypyrimidine (a) 2.5 parts of benzoyl peroxide (containing 25% of water) was suspended in 408 parts of carbon tetrachloride. The mixture was stirred to dissolve the benzoyl peroxide, then dried over magnesium sulphate. To this solution was added 67.5 parts of sulphuryl chloride and the resulting solution was added dropwise over 1.5 hours to a refluxing solution of 42 parts of diketene in 816 parts of carbon tetrachloride. At the end of the addition, the mixture was heated under reflux for a further 1.5 hours, then the carbon tetrachloride was removed at the water pump. Distillation of the residue at 0.01 mb gave 4-chloro-4-chloromethyloxetan-2-one b.p. 35°–36° C. which crystallised on cooling below 20° C.

(b) 620 parts of 4-chloro-4-chloromethyloxetan-2-one and 440 parts of guanidine hydrochloride were charged to a reaction flask and the mixture was stirred and heated under nitrogen purge as the bath temperature was gradually raised to 120° C. When the bath temperature approached 100° C., reaction commenced accompanied by evolution of hydrogen chloride. When the initial reaction subsided after a few minutes the bath temperature was raised to 130° C. and held until the reaction ceased as indicated by cessation of gassing (about 1 hour). The reaction mixture was allowed to cool about 60° C. and 1750 parts of water was added to the syrup. The solution was extracted with 500 parts of ethyl acetate and the extract was discarded. The aqueous phase was treated with decolourising charcoal, filtered and the pH was adjusted to pH 8 by the addition of saturated aqueous sodium bicarbonate solution. The precipitated solid was filtered, washed with water and dried to constant weight at 80° C. in a vacuum oven to give 2-amino-4-chloromethyl-6-hydroxypyrimidine, m.p. 195°–197° C.

$C_5H_6ClN_3O$ requires C, 37.63; H, 3.79; N, 26.33; Cl, 22.22

Found C, 37.54; H, 3.81; N, 26.16; Cl, 22.36

EXAMPLE 2

2-Amino-4-chloromethyl-6-hydroxypyrimidine

A solution of 7.1 parts of chlorine in 80 parts of carbon tetrachloride was added, dropwise, with stirring, to a solution of 8.4 parts of diketene in carbontetrachloride (160 parts) at −20° to −25° C. When the addition was complete, the solution was allowed to warm to 0° C., and the solvent was removed in vacuo at below 20° C. To the residual 4-chloroacetoacetyl chloride was added 19.0 parts of guanidine hydrochloride and the mixture was heated in an oil bath at 100° C. for 1 hour, with stirring. The temperature was raised to 120° C. for 15 minutes and the mixture was then cooled. The product was dissolved in 200 parts of warm water and extracted with 50 parts of ethyl acetate. The extract was discarded and the aqueous phase was stirred with 0.5 parts of decolourising charcoal, filtered and neutralised by the addition of saturated sodium acetate solution. The solid product was filtered, washed with water and dried to give 2-amino-4-chloromethyl-6-hydroxy-pyrimidine identical to that obtained in Example 1.

EXAMPLE 3

2-Amino-4-(2,2-dichlorovinyl)-6-hydroxypyrimidine

119 Parts of 4-chloro-4-(2,2,2-trichloroethyl)-oxetan-2-one and 95.5 parts of guanidine hydrochloride were charged to a reaction flask and heated in an oil bath at 140° C. for 15 minutes. The solid dissolved and HCl gas was evolved. The oil bath temperature was raised to 160° C. and heating was continued for a further 45 minutes. The heat was removed and the reaction mass was stirred until cool and solidified. The solid was stirred with 250 parts of ethyl acetate and filtered. The filtrate was discarded and the solid dissolved in 1000 parts of hot water, treated with charcoal and filtered. The aqueous solution was cooled and neutralised by the addition of saturated sodium acetate solution. The precipitated solid was filtered and washed with water. This crude product was then dissolved in 550 parts of concentrated hydrochloric acid, diluted with 800 parts of water and stirred with 5 parts of charcoal for 20 minutes. The solution was filtered and the product precipitated by the addition of saturated sodium acetate solution to pH 6. The solid was filtered, washed with water and dried in a vacuum oven at 110° C. to give 2-amino-4-(2,2-dichloro-vinyl)-6-hydroxypyrimidine m.p. 245°–248° C. (decomposition).

$C_6H_5Cl_2N_3O$ requires C, 34.98; H, 2.45; N, 20.40

Found C, 35.08; H, 2.35; N, 20.10

EXAMPLE 4

2-Amino-4-chloro-6-chloromethylpyrimidine 47.9 Parts of 2-amino-4-chloromethyl-6-hydroxypyrimidine was added portionwise to 410 parts of phosphorus oxychloride with stirring. The mixture was placed in an oil bath at 130° C. and stirred until all the solid had dissolved and then for a further 10 minutes. The solution was cooled and the excess of phosphorus oxychloride was removed in vacuo. The residual viscous oil was poured onto 300 parts of ice with stirring and the pH of the resulting mixture was adjusted to pH 8 by the portionwise addition of solid sodium bicarbonate. The mixture was extracted four times with diethyl ether. The ether extracts were combined, dried over anhydrous magnesium sulphate and evaporated to give a pale-yellow solid. Recrystallisation from carbon tetrachloride gave pure 2-amino-4-chloro-6-chloromethylpyrimidine m.p. 126°–128° C.

$C_5H_5Cl_2N_3$ requires C, 33.73; H, 2.83; N, 23.60; Cl, 39.83

Found C, 33.80; H, 2.82; N, 23.40; Cl, 40.19

EXAMPLE 5

2-Amino-4-chloro-6-(2,2-dichlorovinyl)pyrimidine

10 Parts of 2-amino-4-(2,2-dichlorovinyl)-6-hydroxypyrimidine and 66 parts of phosphorus oxychloride were heated together under reflux for 1 hour with stirring. The solution was cooled and excess phosphorus oxychloride was removed in vacuo on a rotary evaporator. The residual viscous oil was poured onto ice, with stirring. Solid sodium bicarbonate was added portionwise until the solution had pH 7–8. The precipitated solid was filtered, washed with water and dried. Recrystallisation from aqueous methanol gave 2-amino-4-chloro-6-(2,2-dichlorovinyl)pyrimidine m.p. 119°–120° C.

$C_6H_4Cl_3N_3$ requires C, 32.10; H, 1.79; N, 18.72
Found C, 32.36; H, 1.76; N, 18.67

EXAMPLE 6

2-Amino-4-chloromethyl-6-methoxypyrimidine 8.9 Parts of 2-amino-4-chloro-6-chloromethylpyrimidine was dissolved in 200 parts of dry methanol at 35° C. A solution of sodium methoxide, prepared by dissolving 1.2 parts of sodium in 20 parts of dry methanol, was added dropwise over 1.5 hour. The solution was stirred at room temperature for 3 hours then evaporated in vacuo.

The residue was partitioned between 150 parts of diethyl ether and 100 parts of water. The ether phase was separated, washed three times with water, dried over anhydrous magnesium sulphate, filtered and evaporated. The residue was chromatographed on a silica column, eluted with a mixture of 40°–60° C. petroleum ether and diethyl ether (2:1 respectively) to give 2-amino-4-chloromethyl-6-methoxypyrimidine m.p. 89°–90° C.

$C_6H_8ClN_3O$ requires C, 41.51; H, 4.65; N, 24.21; Cl, 20.42
Found C, 41.48; H, 4.53; N, 23.92; Cl, 19.87

EXAMPLE 7

2-Amino-4-(2,2-dichlorovinyl)-6-methoxypyrimidine 22.0 Parts of 2-amino-4-chloro-6-(2,2-dichlorovinyl)-pyrimidine was dissolved in 500 parts of dry methanol and stirred whilst a solution of sodium methoxide, prepared by dissolving 4.6 parts of sodium in 200 parts of dry methanol, was added dropwise, over 30 minutes at ambient temperature. The resulting solution was stirred for 4 hours by which time all the starting material had been consumed. The product was precipitated by the addition of water, filtered and dried. The solid obtained was purified by chromatography on silica using diethyl ether as eluent. Final purification was effected by recrystallisation from carbon tetrachloride to give 2-amino-4-(2,2-dichlorovinyl)-6-methoxypyrimidine m.p. 90°–91° C.

$C_7H_7Cl_2N_3O$ requires C, 38.20; H, 3.21; N, 19.09
Found C, 38.23; H, 3.09; N, 18.90

EXAMPLE 8

2-Amino-4-chloromethyl-6-dimethylaminopyrimidine 8.1 Parts of dimethylamine hydrochloride was added to a solution of 2.3 parts of sodium in 20 parts of methanol. The resulting mixture was added dropwise with stirring over about 10 minutes to a solution of 9.9 parts of 2-amino-4-chloro-6-chloromethylpyrimidine in 50 parts of methanol. The reaction was monitored by TLC and when reaction was complete the solvent was evaporated and the residue stirred with about 20 parts of water. The solid obtained was filtered and dried. The product was purified by chromatography on silica, eluted with ethyl acetate, followed by sublimation at 110° C./0.04 mb to give 2-amino-4-chloromethyl-6-dimethylaminopyrimidine m.p. 127°–129° C.

$C_7H_{11}ClN_4$ requires C, 45.04; H, 5.94; N, 30.02
Found C, 45.19; H, 5.90; N, 29.78

EXAMPLE 9

2-Amino-4-fluoro-6-fluoromethylpyrimidine

A mixture of 26.7 parts of 2-amino-4-chloro-6-chloromethylpyrimidine, 79.0 parts of caesium fluoride and 200 parts of dry dimethylformamide was stirred under reflux for 2 hours. The mixture was cooled and evaporated in vacuo. The residue was partitioned between ethyl acetate and water and some insoluble solid was removed by filtration. The ethyl acetate phase was separated and the aqueous phase was extracted four times with ethyl acetate. The organic extracts were combined, washed twice with water, dried over magnesium sulphate and evaporated. The crude product was purified by chromatography on silica, eluted with mixtures of ethyl acetate and dichloromethane, the concentration of ethyl acetate being gradually increased from 25% to 80%, to give 2-amino-4-fluoro-6-fluoromethyl-pyrimidine m.p.189°–190° C.

$C_5H_5F_2N_3$ requires C, 41.38; H, 3.48; N, 28.96
Found C, 41.34; H, 3.47; N, 29.07

EXAMPLE 10

2-Amino-4-fluoromethyl-6-methoxypyrimidine

A mixture of 17.0 parts of 2-amino-4-chloromethyl-6-methoxypyrimidine, 59.5 parts of caesium fluoride and 130 parts of dry dimethylformamide was stirred under reflux for 2 hours. The mixture was cooled and evaporated in vacuo. The residue was taken up in ethyl acetate and the solution was washed four times with water. The organic phase was dried with anhydrous magnesium sulphate, stirred with decolourising charcoal, filtered and evaporated. The crude product was purified by chromatography on silica, eluted with ethyl acetate to give 2-amino-4-fluoromethyl-6-methoxypyrimidine m.p. 119°–121° C.

$C_6H_8FN_3O$ requires C, 45.86; H, 5.13; N, 26.74
Found C, 45.83; H, 5.06; N, 26.64

EXAMPLE 11

2-Amino-4-chloro-6-fluoromethylpyrimidine (a) A mixture of 20 parts of 2-amino-4-chloro-6-chloromethylpyrimidine, 70 parts of dry caesium fluoride and 390 parts of dry acetonitrile was stirred under reflux for 17 hours. The mixture was cooled and evaporated in vacuo.

The resulting residue was purified by chromatography on silica, eluted with mixtures of ethyl acetate and dichloromethane, the concentration of ethyl acetate being gradually increased from 25% to 35% to give a mixed product containing 2-amino-4-chloro-6-fluoromethylpyrimidine and 2-amino-4-fluoro-6-fluoromethyl-pyrimidine.

(b) 6.7 parts of a mixture of 2-amino-4-chloro-6-fluoromethylpyrimidine (A) and 2-amino-4-fluoro-6-fluoromethylpyrimidine (B) containing 20% B was suspended in 160 parts of absolute ethanol. To this suspension was added 15.2 parts of 0.5M ethanolic sodium ethoxide dropwise over 15 minutes. The reaction mixture was heated to 45° C. and stirred for a further 30 minutes. Evaporation of the reaction mixture gave a white solid which was partitioned between water and ethyl acetate and the aqueous phase extracted four times with ethyl acetate. The organic extracts were combined, washed with water, dried over magnesium sulphate and evaporated to give a white solid. The white solid product was purified by chromatography on silica, eluted with mixtures of ethyl acetate and dichloromethane, the concentration of ethyl acetate being gradually increased from 25% to 70%. The first fifteen fractions were combined and evaporated to dryness and the solid product so obtained was recrystallised from cyclohexane containing 15% ethyl acetate to give 2-amino-4-chloro-6-fluoromethylpyrimidine m.p. 159° C.

The remaining fractions were combined and evaporated to give a solid (C).

EXAMPLE 12

2-Amino-4-ethoxy-6-fluoromethylpyrimidine

Solid C prepared according to Example 11b was recrystallised from cyclohexane to give 2-amino-4-ethoxy-6-fluoromethylpyrimidine m.p. 85°–87° C.
$C_7H_{10}FNO$ requires C, 49.12; H, 5.89; N, 24.55
Found C, 49.23; H, 5.94; N, 24.65

EXAMPLE 13

2-Amino-4-fluoromethyl-6-methylthiopyrimidine

A mixture of 1.0 part of 2-amino-4-fluoro-6-fluoromethylpyrimidine, 3.0 parts of methanethiol and 50 parts of dry tetrahydrofuran was stirred at 5° C. whilst a solution of 0.16 parts of sodium in 20 parts of dry methanol was added dropwise. The temperature was kept below 10° C. with ice-bath cooling. When the addition was complete, stirring was continued for 1 hour. The resulting solution was evaporated and the residue was diluted with water and extracted three times with 50 parts of ether. The ethereal solutions were combined and dried (MgSO4). The solvent was evaporated and the crude product was purified by recrystallisation from carbon tetrachloride to give 2-amino-4-fluoromethyl-6-methylthiopyrimidine m.p. 95°–97° C.
$C_6H_8FN_3S$ requires C, 41.61; H, 4.66; N, 24.27
Found C, 41.71; H, 4.89; N, 24.24

EXAMPLE 14

2-Amino-4-n-butoxy-6-chloromethylpyrimidine 3,56 Parts of 2-amino-4-chloro-6-chloromethyl-pyrimidine and 2.24 parts of potassium t-butoxide were dissolved in 60 parts of n-butanol at room temperature then the solution was heated at 50° C. for 2 hours, with stirring. After this time, the solution was cooled and evaporated in vacuo. The residue was partitioned between ethyl acetate and water and the organic phase was separated and washed three times with water then dried (MgSO4). Evaporation of the solvent gave the crude product which was purified by chromatography on silica (Merck Kieselgel 60) eluted with ether to give 2-amino-4-n-butoxy-6-chloromethylpyrmidine as an oil.
$C_9H_{14}ClN_3O$ requires C, 50.12; H, 6.54; N, 19.48
Found C, 49.89; H, 6.52; N, 19.50

EXAMPLE 15

2-Amino-4-chloromethyl-6-(N-morpholino)pyrimidine 3.56 Parts of 2-amino-4-chloro-6-chloromethyl-pyrimidine was stirred with 40 parts of dry methanol and a solution of 3.5 parts of morpholine in 12 parts of dry methanol was added dropwise over 10 minutes during which time all the solid dissolved. The solution was stirred at room temperature for 5 hours then left to stand overnight. The solvent was evaporated and the residue was dissolved in ethyl acetate and the solution was washed three times with water, dried (MgSO4) and evaporated. The product was recrystallised from toluene and then further purified by chromatography on silica (Merck Kieselgel 60) eluted first with ether and then with ethyl acetate. Recrystallisation from ethyl acetate gave 2-amino-4-chloro-methyl-6-(N-morpholino)pyrimidine m.p. 138°–140°.
$C_9H_{13}ClN_4O$ requires C, 47.26; H, 5.74; N, 24.50
Found C, 47.34; H, 5.82; N, 24.64

EXAMPLE 16

2-Amino-4-chloromethyl-6-diallylaminopyrimidine 3.56 Parts of 2-amino-4-chloro-6-chloromethyl-pyrimidine and 3.9 parts of diallylamine were reacted together according to the method of Example 15 to give 2-amino-4-chloromethyl-6-diallylaminopyrimidine m.p. 53°–55° C.
$C_{11}H_{15}ClN_4$ requires C, 55.33; H, 6.34; N, 23.47
Found C, 55.34; H, 6.37; N, 23.49

EXAMPLE 17

2-Amino-4-chloro-6-chloromethylpyrimidine hydrochloride 3.56 Parts of 2-amino-4-chloro-6-chloromethyl-pyrimidine was dissolved in 53 parts of dry diethyl ether and dry hydrogen chloride was bubbled through the solution, with stirring, until no further solid precipitated the solid was filtered, washed with ether and dried in vacuo. Recrystallisation from acetone gave 2-amino-4-chloro-6-chloromethyl-pyrimidine hydrochloride m.p. 145°–150° C. (decomposition).
$C_5H_6Cl_3N_3$ requires C, 28.00; H, 2.82; N, 19.59
Found C, 28.05; H, 2.82; N, 19.65

EXAMPLE 18

2-Amino-4-chloromethyl-6-(2,2,2-trifluoroethoxy)-pyrimidine 0.23 Parts of sodium metal was added to 10 parts of 2,2,2-trifluoroethanol with stirring and ice-bath cooling. The mixture was then stirred for several hours at room temperature until the sodium dissolved. This solution was added dropwise, over 30 minutes, to a stirred suspension of 1.78 parts of 2-amino-4-chloro-6-chloromethyl-pyrimidine in 25 parts of 2,2,2-trifluoro-ethanol and the resulting mixture was stirred at 60° C. for 18 hours. A further 0.1 parts of sodium was dissolved in 10 parts of 2,2,2-trifluoroethanol and added to the reaction mixture. Stirring at 60° C. was continued for a further 24 hours then the reaction mixture was cooled and evaporated in vacuo. The residue was partitioned between ethyl acetate and water. The organic layer was separated, washed with water, dried (MgSO4) and evaporated. The crude product was purified by chromatography on silica (Merck Kieselgel 60 using a 50:50 mixture of ether and 40°–60° petroleum ether as eluent followed by recrystallisation from a mixture of 60°–80° petroleum ether and ethyl acetate to give 2-amino-4-chloromethyl-6-(2,2,2-trifluoroethoxy)pyrimidine m.p. 77°–78° C.
$C_7H_7ClF_3N_3O$ requires C, 34.79; H, 2.93
Found C, 34.70; H, 3.04

EXAMPLE 19

2-Amino-6-fluoromethylpyrimidin-4-one 12.1 Parts of 2-amino-4-fluoro-6-fluoromethylpyrimidine was dissolved in 200 parts of 20% aqueous acetic acid at reflux, with stirring. The mixture was heated under reflux for 1 hour then cooled. The precipitated solid was filtered, washed with 50% aqueous acetic acid and then with acetone. The solid was dried in vacuo at 140° C. to give 2-amino-6-fluoromethylpyrimidine-4-one, m.p. 237°–238° C. (decomposition).

'H NMR: (δ, DMSO-d₆); 5.05 (d, 2H); 5.60 (S, 1H); 6.85 (br. s, 2H), D₂O replaceable); 8.60 (br. s, 1H, D₂O replaceable).

We claim:

1. A process for producing a compound of the formula III

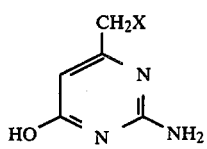

or an acid salt thereof, wherein X is F, Cl or Br, which comprises heating and stirring at 50° to 200° C., in the absence of a base, a mixture of a compound of the formula II

XCH₂COCH₂COX⁰     II wherein X and X⁰ independently, are F, Cl or Br, and guanidine or an quanidine acid salt.

2. A process of claim 1, wherein the compound of formula II is heated with an excess of a guanidine acid salt, in the absence of a solvent, at a temperature within the range of from 100° to 120° C.

3. A process of claim 1, wherein the salt of the compound of formula III is the hydrochloride, sulphate, perchlorate, phosphate, methanesulphonate, trifluoroacetate or paratoluene sulphonate.

4. A process of claim 1 wherein X⁰ is Cl.

5. A process of claim 1, wherein the reaction to produce the compound of formula III is carried out at 100° to 120° C.

* * * * *